United States Patent
Peng et al.

(10) Patent No.: US 8,237,110 B2
(45) Date of Patent: Aug. 7, 2012

(54) ION MOBILITY SPECTROMETER DETECTION METHOD USING DOPANTS

(75) Inventors: Hua Peng, Beijing (CN); Hui Li, Beijing (CN); Zhongxia Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 72 days.

(21) Appl. No.: 12/994,293

(22) PCT Filed: Jul. 2, 2010

(86) PCT No.: PCT/CN2010/074932
§ 371 (c)(1),
(2), (4) Date: Nov. 23, 2010

(87) PCT Pub. No.: WO2011/035633
PCT Pub. Date: Mar. 31, 2011

(65) Prior Publication Data
US 2011/0297821 A1 Dec. 8, 2011

(30) Foreign Application Priority Data
Sep. 25, 2009 (CN) .......................... 2009 1 0093179

(51) Int. Cl.
*H01J 49/40* (2006.01)
(52) U.S. Cl. ........................................ 250/286; 250/288
(58) Field of Classification Search .................. 250/286, 250/287, 288
See application file for complete search history.

(56) References Cited

U.S. PATENT DOCUMENTS
3,699,333 A 10/1972 Cohen et al. ................. 250/41.9
(Continued)

FOREIGN PATENT DOCUMENTS
CN 1657899 A 8/2005
(Continued)

OTHER PUBLICATIONS
German Office Action from German Application No. 112010000007.7, dated Feb. 27, 2012, 6 pages.
(Continued)

*Primary Examiner* — Kiet T Nguyen
(74) *Attorney, Agent, or Firm* — Westman, Champlin & Kelly, P.A.

(57) ABSTRACT

Disclosed is an ion mobility spectrometer (IMS) detection method using dopants. The ion mobility spectrometer comprises a sample feeding device, a drift tube and a gas passage system communicated therewith. The gas passage system comprises a pump, a filtering device, a gas inlet and a gas outlet provided on the drift tube for providing clean gas used as the drift gas and the sample carrier gas. The detection method comprises: providing a sampling substrate for sample collection; combining the dopants with the sampling substrate; collecting the sample using the sampling substrate combined with the dopants; and introducing the sampling substrate that has collected the sample into the sample feeding port of the ion mobility spectrometer for detection. With this method, it is unnecessary to provide an independent dopant gas passage, thereby simplifying the structure of the instrument and meanwhile, making it easier and more accurate to control the amount of the dopants required for detection.

14 Claims, 4 Drawing Sheets

U.S. PATENT DOCUMENTS

| | | | | |
|---|---|---|---|---|
| 4,311,669 | A | 1/1982 | Spangler | 422/98 |
| 4,551,624 | A | 11/1985 | Spangler et al. | 250/287 |
| 4,777,363 | A | 10/1988 | Eiceman et al. | 250/286 |
| 5,032,721 | A | 7/1991 | Bacon et al. | 250/282 |
| 5,234,838 | A | 8/1993 | Bacon, Jr. | 436/173 |
| 5,283,199 | A | 2/1994 | Bacon, Jr. et al. | 436/173 |
| 5,491,337 | A | 2/1996 | Jenkins et al. | 250/287 |
| 6,495,824 | B1 | 12/2002 | Atkinson | 250/287 |
| 6,642,513 | B1 * | 11/2003 | Jenkins et al. | 250/288 |
| 2002/0088936 | A1 | 7/2002 | Breach et al. | 250/281 |
| 2005/0167583 | A1 | 8/2005 | Miller et al. | |

FOREIGN PATENT DOCUMENTS

| | | |
|---|---|---|
| CN | 101169389 A | 4/2008 |
| CN | 201242505 Y | 5/2009 |
| CN | 201247223 Y | 5/2009 |
| CN | 101473221 | 7/2009 |
| DE | 19502674 | 1/1995 |
| DE | 19609582 | 3/1996 |
| DE | 10212110 | 3/2002 |
| EP | 0509171 | 7/1991 |
| EP | 1672363 | 5/2001 |
| WO | WO9306476 | 4/1993 |
| WO | WO2004102611 | 11/2004 |
| WO | WO2006123107 | 11/2006 |
| WO | WO2006129101 | 12/2006 |
| WO | WO2007082941 | 7/2007 |
| WO | WO2007085898 | 8/2007 |
| WO | 2008/053181 A1 | 5/2008 |
| WO | WO2008107640 | 9/2008 |
| WO | WO2008110754 | 9/2008 |
| WO | WO2009018305 | 2/2009 |
| WO | WO2009069000 | 6/2009 |

OTHER PUBLICATIONS

English translation for German Office Action dated Feb. 27, 2012 for German Application No. 112010000007.7, 4 pages.

Chinese Office Action for Chinese Application No. 200910093179.9, dated Mar. 31, 2012, 6 pages.

* cited by examiner

ION MOBILITY SPECTROMETER DETECTION METHOD USING DOPANTS

CROSS-REFERENCE TO RELATED APPLICATIONS

This application claims the benefit of PCT international application PCT/CN2010/074932, which was filed on Jul. 2, 2010, and which is incorporated herein in its entirety by reference.

BACKGROUND OF THE INVENTION

1. Field of the Invention

The present disclosure relates to an ion mobility spectrometer detection method using dopants.

2. Description of the Related Art

Ion mobility spectrometry (IMS) has been proposed and developed as a trace detection technique since the 1960s. Earlier patents (U.S. Pat. Nos. 3,699,333 and 4,777,363) described the gist of this technique in details. The operation of an ion mobility spectrometer is based on the following principles: sample vapor or vaporized solid sample particles to be detected are ionized to form ions which then migrate directedly through a drift tube under the influence of a weak electric field. A collector provided at an end of the drift tube is used to measure the drift times taken by the ions to pass through the electric field, so that mobilities of the ions i.e., drift velocities of the ions under the influence of per unit electric field intensity, can be calculated from the drift times taken by the ions. Since the mobilities of ions obtained from various substances are specific under certain conditions depending upon the mass the number of charges and the space structure of the ions, the types of the substances can be determined by matching the detected mobility values of the resultant ions with those collected in a standard library.

The drift tube is the core component of an ion mobility spectrometer, the basic structure of which is shown in FIG. 1, comprising a sample inlet, an ionization region, an ion gate, a drift region and a collector etc.

At the forefront of the drift tube is provided the sample inlet into which the sample to be detected is introduced and carried by a carrier gas to the ionization region. Purified air is usually used as the carrier gas. Electrons emitted from an ion source 63Ni in the ionization region will react with $N_2$ or $O_2$ comprising the air and a small amount of water molecules present in the air to generate reactant cluster ions, such as $(H_2O)_nH^+$, $(H_2O)_nNO^+$, $(H_2O)_nNH_4^+$, $(H_2O)_nO_2^-$, $(H_2O)_n(CO_2)mO_2^-$, $(H_2O)_nOH^+$, etc. When entering into the ionization chamber, molecules of a substance to be detected or a sample will react with the reactant ions to form product ions. When the ion gate is opened, the product ions enter into the drift region from the ionization region, migrate directedly under the influence of the electric field, and finally impinge onto the collector disposed at the end of the drift region opposite to the ionization chamber. In this way, weak current signals representing the strength of ion flows are generated, and the resultant spectrum shows real-time information indicating variation of ion strength with time. Since the mobilities of various product ions are different from each other, the drift times required to reach the collector also vary from each other. By analyzing the spectra and matching the spectra with those collected in the standard library, the type of the substance can be determined.

The ionization of gas molecules of the sample to be detected, which occurs in the ionization region of the drift tube, is regarded as a process of secondary ionization. The concentration ratio of the carrier gas to the sample vapor causes the molecules of the carrier gas to be more easily ionized by the ion source than the molecules of the sample vapor. Therefore, air molecules first undergo ionization to form reactant ions. Since the free path for the ionized molecules of the carrier gas is much shorter than the geometrical size of the ionization chamber, the ionized molecules of the carrier gas will collide with the sample vapor molecules frequently, thereby leading to the transfer of electric charges or protons from the ionized molecules of the carrier gas to the sample molecules. The occurrence of such transfer reaction of electric charges or protons depends on proton or electron affinity of the molecules participating in the reaction. The electric charges will be transferred from the molecules having small electron or proton affinities to those having large electron or proton affinities.

For an ion mobility spectrometer in actual use, the addition of dopants is usually adopted to modify molecule composition of the reactants and the ionization mechanisms so that chemical composition of the resultant product ions can be changed to improve the sensitivity and selectivity of the instrument, It is necessary that the dopant molecules have an electron affinity less than that of the sample molecules (e.g., explosives) and higher than that of other components contained in the carrier gas. Thus, cluster ions having relatively stable composition can be preferably generated through ionization to prevent interferences with lower affinities in the carrier gas from participating in the ionization reaction. Meanwhile, since the electron or proton affinity of the sample molecules is greater than that of the dopant molecules, these cluster ions then react with the sample vapor molecules to form the sample molecule ions for detection. The addition of dopants can cause a shift in peak positions corresponding to the resultant product ions in the spectrum. In this way, the ion peaks, which can be hardly distinguished due to peak overlap in a case where no dopant is added, can be separated from each other to realize identification of the target components even in the presence of interferents. The currently common-used dopants for the detection of explosives are halogenated compounds, and the dopants usually used for drug detection include nicotinamide, acetone, ammonia water or the like.

Over the past thirty years, a large amount of research on IMS techniques has been made in the developed countries, and a great number of patents, such as U.S. Pat. No. 4,311,669, U.S. Pat. No. 4,551,624, DE Pat. No, 19502674, WO Pat. No. 9306476, etc., involving structural design, separation principle, and sampling techniques have been issued. Some of these patents describe the methods of adding dopants and the associated applications.

PCT patents, for example, WO Pat. No. 2006129110 and WO Pat. No. 2004102611 discloses ways of adding chemical dopants. The ion mobility spectrometer disclosed in PCT patent WO Pat. No. 2006129101 employs at least two reservoirs for supplying various dopants. The reservoirs are connected with an ionization chamber of the instrument. An inlet port is provided at a side of a selectively permeable membrane facing a sample inlet. Thus, the sample gas is brought into contact with the dopants before being ionized. The circulation gas passage in the drift tube and the doping gas passage are separated from each other. The system disclosed in PCT patent WO Pat. No. 2004102611 comprises a molecular sieve doped with a dopant which can be used to continuously supply a first dopant. The system further comprises additional reservoirs containing various dopants to selectively supply other dopants in addition to the first dopant into the air by means of switches.

Furthermore, the apparatus disclosed in U.S. Pat. No. 6,495,824 comprises a plurality of reservoirs containing various dopants to selectively add different dopants into the flow of the carrier gas according to changes in detection signals. The added dopants react with samples to generate resultant adduct products having different mobilities. An information library, containing known reaction information of an substance to be detected with different dopants, can be established. By comparing between the observation results and the data in the information library for specific combination of the sample and various dopants, it can be determined whether the sample contains the substance to be detected. In patent WO/2007/082941, it is disclosed that a substance to be analysed is injected by means of an atmospheric pressure ionization interface at the inlet of the instrument and meanwhile an additive is introduced by adding it to the nebulizing gas. A doping source material is combined with a material for drying and cleaning the circulation gases/vapors as is shown in U.S. Pat. No. 2002088936. In U.S. Pat. No. 5,491,337, it is disclosed that a low concentration of dopant is mixed with a carrier gas in an enclosed container disposed in front of a sample gas inlet of the instrument, and then is introduced, together with the sample gas, into the ionization chamber. As disclosed in In EP Pat. No. 1672363, the sample gas is mixed with the doping gas before entering into the instrument, or the doping gas is added into the drift gas, so as to eliminate the problem caused by interference when the ion mobility spectrometer is used to analyze a large number of inert gas samples.

Patents WO2006/123107, EP 0509171, U.S. Pat. No. 5,283,199, U.S. Pat. No. 5,234,838, U.S. Pat. No. 5,032,721, DE 19609582, DE 10212110, WO2007/085898, etc., describe various dopants used for analysis by ion mobility spectrometry to adapt to different applications. A dopant containing diamyl ketone, for example, is added into a circulation gas passage. A small amount of a dopant sulphur dioxide, for example, is added into a sample to be detected by means of a temperature-controlled permeable tube. Acetone and carbon tetrachloride, for example, can be added as dopants into the carrier gas before the sample is injected. A small amount of substituted phenol dopants (e.g., methyl salicylate, 2-hydroxy hypnone) and amine dopants (e.g., methylamine), for example, are added into a sample to be detected by means of a temperature-controlled permeable tube. The content of ammonia gas in gas mixtures, for example, is monitored by using dimethyl methylphosphonate (DMMP) as the dopant. Amides, for example, are supplied as ionization dopants to generate reactant ions and then interact with a substance to be detected for the detection of peroxide explosives.

FIG. 2 depicts a schematic view of the structure of an ion mobility spectrometer system using a dopant in the prior art.

The detection system comprises a sample feeding port 21, a drift tube 20 containing an ion source 10, and a gas passage system communicated with the drift tube. A dopant gas source 41 is used for supplying a dopant gas that is added into the system by the carrier gas or the drift gas. A sampling substrate is used for collecting a certain amount of a sample and is guided, together with the collected sample, into the sample feeding port of the drift tube. Thereinto, the gas passage system comprises a pump (not shown) and a filter 34. Outlet of the gas passage system is communicated with a gas inlet 31 disposed at an end of a drift region opposite to an ionization region and a gas inlet 32 disposed at a position in the ionization region which is adjacent to an ion source, respectively, to supply a clean gas flow used as the drift gas and the sample carrier gas, such as air. An inlet of the gas passage system is communicated with a gas outlet 33 disposed at a position in the ionization region which is adjacent to an ion gate, to guide the unionized drift gas and carrier gas molecules out of the drift tube. Then, the unionized drift gas and carrier gas molecules are dried and purified to be used for circulation in the gas passage system. Arrangements of the dopant gas source 41 in the gas passage, i.e., ways of adding the dopant, can be varied. The dopant gas source 41 can be arranged in the carrier gas passage connected to the gas inlet 31 or in the drift gas passage connected to the gas inlet 32. The obtained dopant vapor is mixed with the drift gas or the carrier gas to enter into the drift tube. Alternatively, the dopant gas source 41 can be combined with a drying and cleaning device and also can be connected with a sample feeding device (not shown). Usually, the sample feeding port and the ionization region are separated from each other by a selectively permeable membrane. A doping inlet is provided at a side of the selectively permeable membrane facing the sample feeding port, so that the sample gas is brought into contact with the dopant before ionization.

In the prior art, in addition to a gas source made of semipermeable membrane to contain a dopant, it is also necessary to control the temperature of the gas source to supply a certain amount of the dopant maintaining a proper concentration. Thus, the gas passage structure and the equipment design become complicated. Furthermore, since the dopant is continuously supplied by a single gas passage, it's difficult to realize the rapid and accurate control of the amount of the dopant, which is easily caused to be either over high due to the accumulation of the dopant in the system or over low due to the depletion or agglomeration of the dopant in its source, thereby affecting the sensitivity of the detection. Additionally, since most of the dopants are corrosive substances, the dopant gas source, the gas passage and associated accessories need to be made of corrosion-resistant material. This undoubtedly increases the manufacturing and maintaining cost of the detection system.

SUMMARY OF THE DISCLOSURE

In view of the technical problems mentioned in the above, this disclosure aims to overcome at least one aspect of defects and problems existing in the prior art.

An object of this disclosure is to provide an ion mobility spectrometer (IMS) detection method using dopants, in which it is unnecessary to provide a dopant gas source in a gas passage system, thereby avoiding the drawbacks of requiring complicate gas passage system design and gas passage parts made of highly corrosion-resistant materials due to the addition and usage of the dopant Another object of this disclosure is to provide a detection method by means of an ion mobility spectrometer (IMS) using a dopant, in which a proper dose of the dopant is combined with a sampling substrate and is introduced, together with a sample, into the spectrometer by sampling and sample feeding operations, thereby achieving a similar dopant addition effect as in a case where the dopant gas source is provided in the system, and thereby avoiding the defect existing in the prior art that it is difficult to accurately control the amount of the dopant due to the accumulation of the dopant in the system.

A further object of this disclosure is to provide an ion mobility spectrometer (IMS) detection system using a dopant, in which it is unnecessary to provide a dopant gas source in a gas passage, thereby simplifying the whole structure of the spectrometer and reducing the manufacturing cost of the system.

According to an aspect of this disclosure, a detection method using an ion mobility spectrometer (IMS) with a dopant is provided. The said ion mobility spectrometer comprises a drift tube having a sample feeding port and a gas passage system communicated therewith. The gas passage system comprises a pump, a filtering device, a gas inlet and a gas outlet provided on the drift tube for providing a clean gas used as the drift gas and the sample carrier gas. The said detection method comprises providing a sampling substrate for sample collection, combining the dopant with the sampling substrate, collecting a sample using the sampling substrate combined with the dopant, and guiding the sampling substrate that has collected the sample to the sample feeding port of the ion mobility spectrometer for detection.

Preferably, the said method of combining the dopant with the sampling substrate comprises the following steps: preparing a solution of the dopant, soaking the sampling substrate into the dopant solution, and taking the sampling substrate out and drying and storing it in an enclosed environment.

Preferably, the said method of combining the dopant with the sampling substrate comprises the following steps: preparing a solution of the dopant, and adding droplets of the dopant solution to a sample collecting region of the sampling substrate.

Preferably, the said dopant includes halogenated hydrocarbons and nicotinamide.

Preferably, the said halogenated hydrocarbons is trichloromethane of which a solution is prepared to have a hundred percent of purity.

Preferably, the gas passage system comprises two gas inlets provided on the drift tube, through which a clean gas is supplied to be used as the drift gas and the sample carrier gas, respectively, and a gas outlet provided on the drift tube to guide the unionized drift gas and carrier gas molecules out of the drift tube.

This disclosure also provides an ion mobility spectrometer (IMS) detection system using a dopant. The detection system comprises an ion mobility spectrometer including a sample feeding port, a drift tube containing an ion source, and a gas passage system communicated with the drift tube. which comprises a pump, a filtering device, and a gas inlet and a gas outlet provided on the drift tube for supplying a clean gas used as the drift gas and the sample carrier gas, a sampling substrate for collecting the sample to be detected, and a dopant which is combined with the sampling substrate to be introduced, together with the sampling substrate that has collected the sample, into the sample feeding port of the drift tube.

With the detection method/system according to this disclosure, the whole structure of the instrument is simplified and the dose of the dopant can be accurately controlled.

BRIEF DESCRIPTION OF THE DRAWINGS

These and/or other aspects and advantages of this disclosure will be apparent and can be easily understood upon reference to the following description of the preferred embodiments in conjunction with the accompanying drawings, in which.

DETAILED DESCRIPTION OF THE PREFERRED EMBODIMENT

The present invention will be explained below with reference to specific embodiments. One skilled in the art can easily understand the structure, advantages and effects of this disclosure from the disclosure of the following embodiments.

Figure 4:
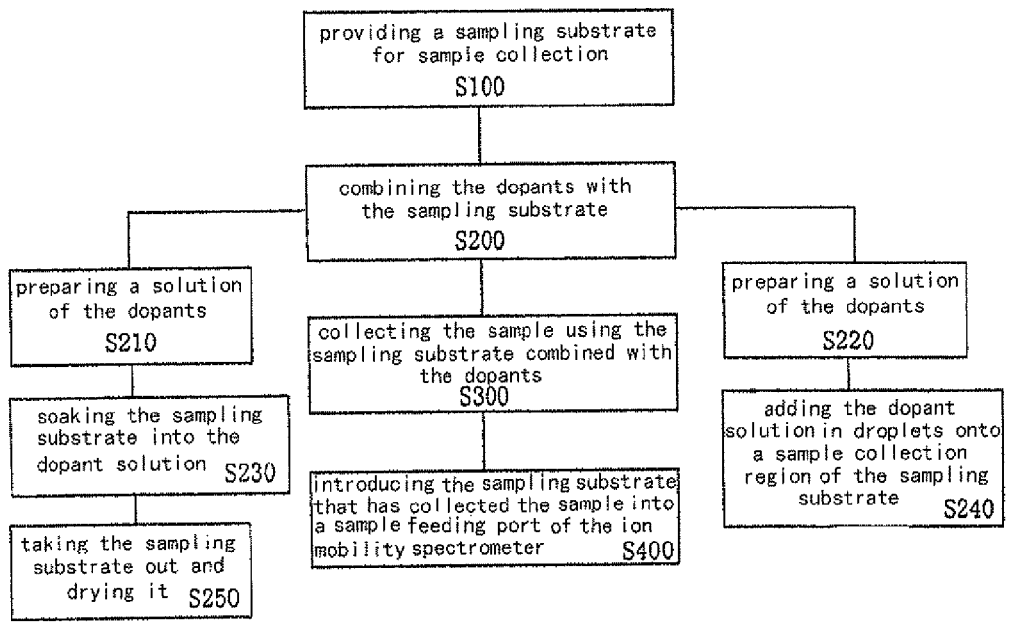
FIG. 4 shows a schematic flow chart of an embodiment of the IMS detection method in accordance with the invention.

Referring to FIG. 4, the flow chart of an ion mobility spectrometer (IMS) and method for using dopants will be explained as below.

In the ion mobility spectrometer (IMS) detection method using a dopant according to the present invention, the ion mobility spectrometer employed comprises a sample feeding device, a drift tube, and a gas passage system communicated with the drift tube (which will be described with reference to FIG. 3 later). Referring to FIG. 4, the detection method according to this invention comprises the following steps: providing a sampling substrate for sample collection at step S100; combining the dopant with the sampling substrate at step S200; collecting the sample using the sampling substrate combined with the dopant at step S300; and introducing the sampling substrate that has collected the sample into a sample feeding port of the ion mobility spectrometer for detection at step S400.

At step S100, the sampling substrate is provided. The sampling substrate may be any suitable substrate known in the prior art made of knitwear, cotton fabric, Teflon, glass yarn or glass fiber, and the like. The sampling substrate itself should not contain any contamination source and should not be dyed and colored. Furthermore, there should be no fiber or cotton thread to drop off during operation. The material for the substrate should be high temperature-resistant, have good chemical inertness, mechanical strength and deformation elasticity, and be easy to be used for sampling and sample-feeding operations. Also, the material may be chemically treated to improve its absorption capability for the sample and to enhance its desorption efficiency.

At step S200, the above-mentioned sampling substrate is combined with a dopant to be used for detection. Such combination can be performed by various ways. As shown, for example, at steps S210, S230, and S250 on the left side of FIG. 4, a solution of the dopant is first prepared having a certain concentration including a concentration of 100% (pure dopant in a liquid state), and then, the specific sampling substrate provided at step S100 is soaked into the dopant solution for a predetermined time; and finally, the soaked sampling substrate is taken out of the dopant solution and is put into an enclosed container to be dried. After that, the dried sampling substrate is quickly sealed for future use.

Alternatively, the above-mentioned combination can be performed as shown at steps S220 and S240 on the right side of FIG. 4. A solution of the dopant is first prepared having a certain concentration including a concentration of 100% (pure dopant in a liquid state) and is sealed into a dedicated reagent bottle. Then, the appropriate dose of the dopant solution is applied to a sample collecting region of the sampling substrate before detection.

As presented in the Description of the Related Art, since the dose of the dopant will influence the separation effect of the ion peaks in the resulting detection spectra, it is necessary to combine the sampling substrate with an appropriate amount of the dopant at step S200. Obviously, if the combination is performed through steps S210, S230 and S250 on the left side of FIG. 4, the sampling substrate combined with the appropriate amount of the dopant can be achieved by changing the concentration of the dopant solution prepared at step S210, the type of the material for the sampling substrate provided at step S230, and the soaking duration at step S250. If the steps on the right side of FIG. 4 are performed, suitable combination of the sampling substrate with the dopant can be achieved by changing the concentration of the dopant solution prepared at step S210 and/or the amount of the dopant solution applied onto the sample collecting region of the sampling substrate.

Subsequently, as described in step S300, the sample is collected using the sampling substrate combined with the appropriate amount of the dopant. During this process, although the sampling substrate used contains the dopant, which is different from the sampling substrate known in the prior art, the collection operation is substantially identical with that known in the prior art. Therefore, the detailed explanation for step S300 is omitted herein.

Finally, as described in step S400, the sampling substrate that has collected the sample is introduced into the sample feeding port of the ion mobility spectrometer (to be described hereinafter) to obtain the spectrum.

A structure of an ion mobility spectrometer detection system using a dopant in accordance with this invention is described below with reference to FIG. 3.

The said ion mobility spectrometer detection system comprises an ion mobility spectrometer comprising a sample feeding port 210, a drift tube 200 containing an ion source 100, and a gas passage system communicated with the drift tube, a sampling substrate for collecting a sample to be detected, and a dopant, which is combined with the sampling substrate so as to be introduced, together with the sampling substrate that has collected the samples, into the sample feeding port of the drift tube.

In order to be easily compared with the prior art introduced in the Description of the Related Art, the gas passage system in accordance with this invention employs, but is not limited to, a carrier gas passage and a drift gas passage which have the same structures as those known in the prior art. Specifically, the gas passage system in accordance with this invention comprises a pump (not shown) and a filtering device 340. The outlet of the gas passage system is communicated with a gas inlet 310 disposed at an end of a drift region opposite to an ionization region and a gas inlet 320 disposed at a position in the ionization region which is adjacent to the ion source, respectively, to supply clean air used as the drift gas and the sample carrier gas. The inlet of the gas passage system is communicated with a gas outlet 330 disposed at a position in the ionization region which is adjacent to an ion gate, to guide unionized drift gas and carrier gas molecules out of the drift tube. Then, the unionized drift gas and carrier gas molecules are dried and purified to be used for circulation in the gas passage system.

Compared with the prior art, in this disclosure, (1) there is no need to provide a dopant gas source in the gas passage system and (2) the sampling substrate introduced into the sample feeding port of the drift tube contains not only the sample carried therewith, but also an appropriate amount of the dopant.

Figure 1:
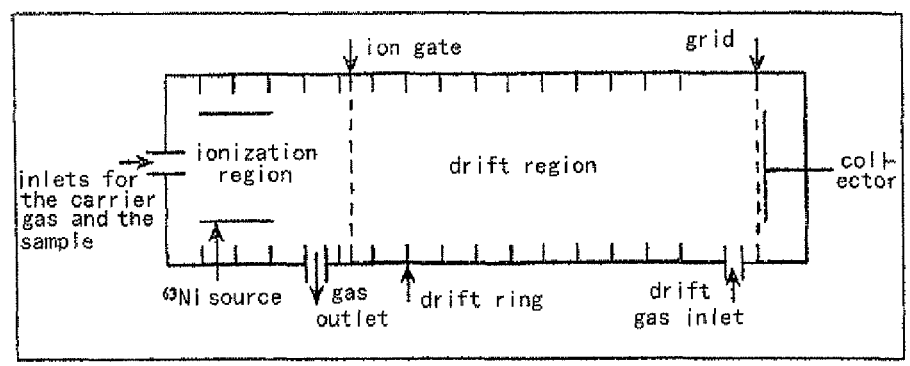
FIG. 1 shows a schematic view of the basic structure of the drift tube.
Figure 2:
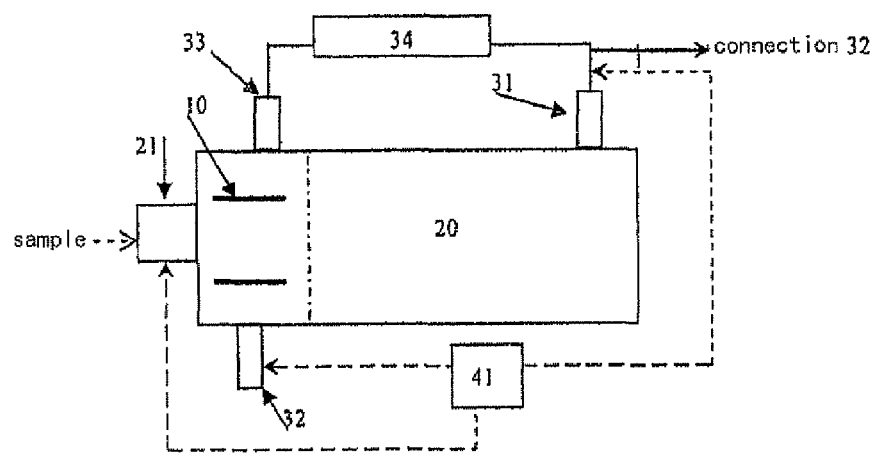
FIG. 2 shows a schematic view of the structure of the ion mobility spectrometer in the prior art.
Figure 3:
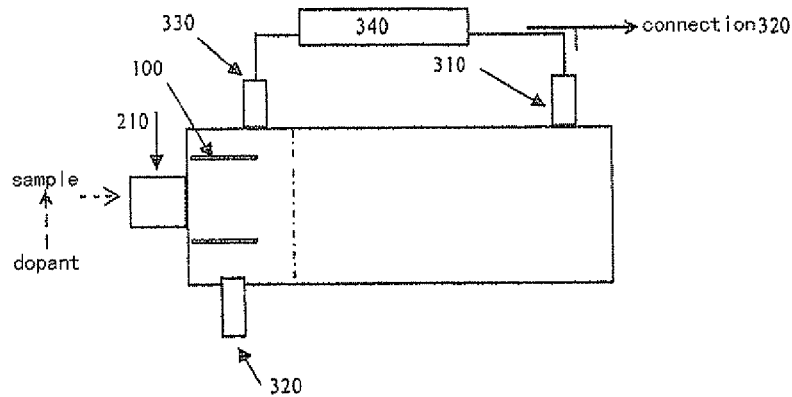
FIG. 3 shows a schematic view of the structure of the ion mobility spectrometer according to the invention.

With reference to FIGS. 4 and 3, the structure of the IMS system and the flow chart of the detection method thereof according to this invention are schematically described. The detection method/system according to this invention creatively combines the sampling substrate with the dopant, thereby leading to a simplified whole structure of the system and easier and more accurate control of the dose of the dopant.

As introduced in the Description of the Related Art, the ion mobility spectrometer detection method/system in accordance with this invention may be applied to various fields, such as the detection for drugs, explosives, and chemical warfare agents. Since different application fields involve different target substances, various types of dopants are used, including halogenated hydrocarbons such as trichloromethane and amides such as nicotinamide, etc.

A description is provided below to explain how to combine the sampling substrate with the dopant in the detection method in accordance with the present invention, i.e., how to realize step S200 in FIG. 4 by taking Hexogen (RDX) as a sample example and trichloromethane as a dopant example.

Alternatively, following the process shown on the right side of FIG. 4, trichloromethane having 100% concentration is also first obtained, and then, a certain volume of trichloromethane primary liquid is dropped using a pipette onto a sample collecting region of the sampling substrate made of fiber material.

In the above example, one skilled in the art can understand that since the dopant used during detection may be a liquid dopant, such as dichloroethene and trichloromethane, or a solid dopant, such as hexachloroethane and nicotinamide, etc., a solid dopant dissolved in a suitable solvent is used in most cases, although the primary liquid can be used in a case where liquid trichloromethane is taken as a dopant. Furthermore, even for a liquid dopant, it is also possible to use a solution with a lower concentration instead of a primary liquid, in consideration of doping dose and so on.

By taking Hexogen (RDX) as a sample example and trichloromethan as a dopant example, comparisons between ion mobility spectra obtained before and after the combination of the sampling substrate with the dopant performed by following the process on the right side of FIG. 4, according to the detection method of this disclosure, are depicted with reference to FIGS. 5a-5d. In the spectra, the horizontal coordinate indicates drift time, and the vertical coordinate indicates ion current strength. By comparing the results before and after combining the dopant with the sampling substrate, improvement on the sensitivity and selectivity for the detection of RDX caused by the addition of the dopant can be observed.

Figure 5A:
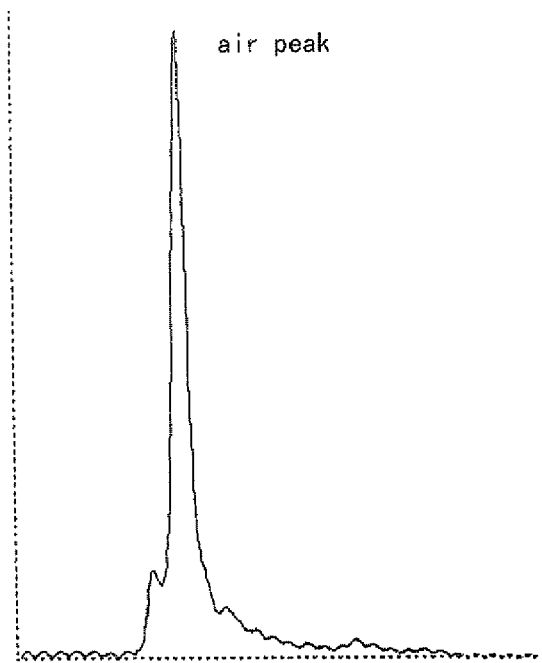
FIGS. 5a-5d show effect comparisons of the detected spectra obtained from an embodiment of the IMS detection method in accordance with the invention.

FIG. 5a shows a detection spectrum obtained when no sampling substrate carrying both the dopant and the sample is introduced, which only contains a reactant ion peak corresponding to the air molecules.

Figure 5B:
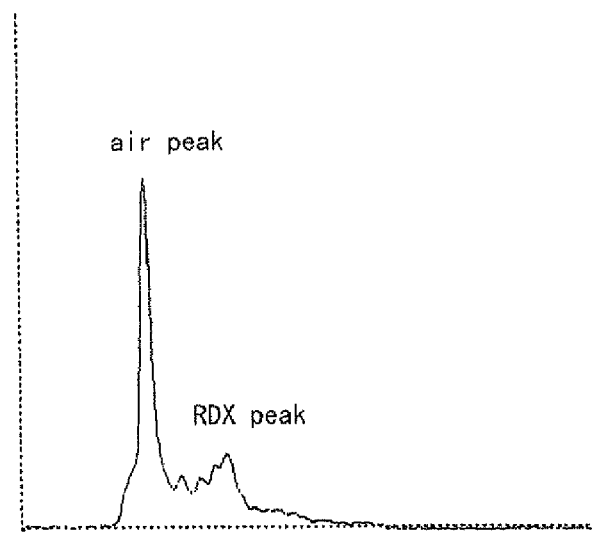

FIG. 5b shows a detection spectrum obtained by applying a certain amount of RDX sample to a sampling substrate which is not combined with the dopant and then introducing the sampling substrate into the sample feeding port of the spectrometer, in which a RDX sample peak can be observed in addition to the reactant ion peak corresponding to the air molecules.

Figure 5C:
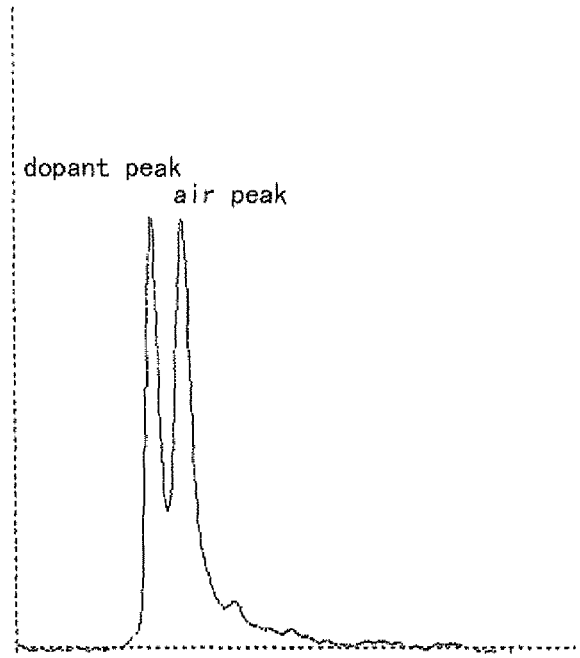

FIG. 5c shows a detection spectrum obtained by introducing a sampling substrate, which has been combined with the dopant and is not supplied with the sample, into the sample feeding port of the spectrometer, in which the reactant ion peak corresponding to the air molecules and the reactant ion peak corresponding to the dopant molecules with substantially the same height.

Figure 5D:
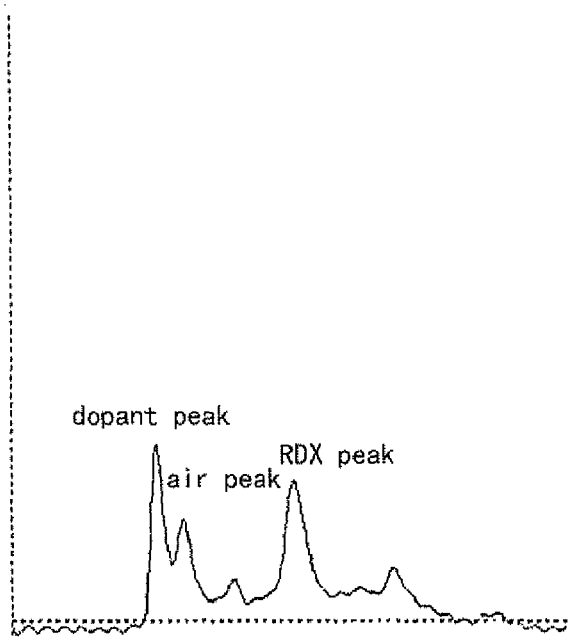

FIG. 5d shows a detection spectrum obtained from the introduction of a sampling substrate combined with the dopant and containing the same amount of the RDX sample as that in FIG. 5b, in which the height of the RDX peak is remarkably increased and the shape of the peak is remarkably improved due to the addition of the dopant.

It can be seen from FIGS. 5a-5d that the detection method in accordance with this invention can provide spectra with good separation effects. Obviously, for other samples and their corresponding dopants, an accurate detection can also be achieved by properly adjusting the amount of the dopant to be combined with the sampling substrate. It is appreciated for one skilled in the art that two dopants which are mutually soluble with each other and do not react with each other can be used as a solution having a "corresponding concentration or suitable concentration" to soak the sampling substrate. The combination can also be achieved by dropping the dopant solution onto the sampling substrate which has been soaked in the corresponding solvent to adapt to the case where various dopants are required during detection. In this case, although the combination process may be complicated, it is still significant in consideration of the simplification of the whole structure of the detection system along with easy and accurate control of the dopant. In light of teaching from the above-described embodiments, one skilled in the art can know operational parameters in other combination processes including the composition of a dopant solution, soaking duration and so on, through limited number of experiments.

Therefore, "the combination of a sampling substrate with dopants" in accordance with the present invention is not limited to the one-off combination with trichloromethane as described in the embodiment, but comprises single or multiple combinations with other dopants known in the prior art. Furthermore, it is not limited to the combination with liquid dopants, but comprises the combination with dopants in any state.

What is claimed is:

1. An ion mobility spectrometer (IMS) and detection method using dopants, wherein the ion mobility spectrometer comprises a drift tube having a sample feeding port and a gas passage system communicated therewith, wherein the gas passage system comprises a pump, a filtering device, and a gas inlet and a gas outlet provided on the drift tube for providing clean gas used as a drift gas and a sample carrier gas, and the detection method comprises the steps of:
   providing a sampling substrate for sample collection;
   combining the dopants with the sampling substrate;
   collecting the sample using the sampling substrate combined with the dopants; and
   introducing the sampling substrate that has collected the sample to the sample feeding port of the ion mobility spectrometer for detection.

2. The detection method according to claim 1, wherein combining the dopants with the sampling substrate comprises the following steps:
   preparing a solution of the dopants, soaking the sampling substrate into the dopant solution, and taking the sampling substrate out and drying it.

3. The detection method according to claim 2, wherein substances used for dopants include halogenated hydrocarbons, nicotinamide, acetone, and ammonia water.

4. The detection method according to claim 3, wherein a representative halogenated hydrocarbon is trichloromethane of which a solution is made to have a hundred percent of purity.

5. The detection method according to claim 3, wherein the gas passage system comprises:
   two gas inlets provided on the drift tube, through which clean gas used as the drift gas and the sample carrier gas is supplied, respectively, and a gas outlet provided on the drift tube to guide the unionized drift gas and carrier gas molecules out of the drift tube.

6. The detection method according to claim 5, wherein the carrier gas comprises pure nitrogen or purified air.

7. The detection method according to claim 1, wherein combining the dopants with the sampling substrate comprises the following steps:
   preparing a solution of the dopants, and adding the dopant solution in droplets onto a sample collecting region of the sampling substrate.

8. The detection method according to claim 7, wherein substances used for dopants include halogenated hydrocarbons, nicotinamide, acetone, and ammonia water.

9. The detection method according to claim 8, wherein a representative halogenated hydrocarbon is trichloromethane of which a solution is made to have a hundred percent of purity.

10. The detection method according to claim 8, wherein the gas passage system comprises:
    two gas inlets provided on the drift tube, through which clean gas used as the drift gas and the sample carrier gas is supplied, respectively, and a gas outlet provided on the drift tube to guide the unionized drift gas and carrier gas molecules out of the drift tube.

11. The detection method according to claim 10, wherein the carrier gas comprises pure nitrogen or purified air.

12. An ion mobility spectrometer (IMS) detection system using dopants, comprising:
    an ion mobility spectrometer including an ion source, a drift tube having a sample feeding port, and a gas passage system communicated with the drift tube, wherein the gas passage system comprises a pump, a filtering device, a gas inlet and a gas outlet provided on the drift tube for supplying clean air used as a drift gas and a sample carrier gas;
    a sampling substrate for collecting a sample to be detected; and
    dopants combined with the sampling substrate to be introduced, together with the sampling substrate that has collected the sample, into the sample feeding port of the ion mobility spectrometer.

13. The detection system according to claim 12, wherein the gas passage system comprises:
    two gas inlets provided on the drift tube, through which clean gas used as the drift gas and the sample carrier gas is supplied, respectively, and a gas outlet provided on the drift tube to guide the unionized drift gas and carrier gas molecules out of the drift tube.

14. The detection system according to claim 13, wherein the carrier gas comprises pure nitrogen or purified air.

* * * * *